US 6,655,380 B1
United States Patent
Andersson et al.

(10) Patent No.: US 6,655,380 B1
(45) Date of Patent: *Dec. 2, 2003

(54) INHALATION DEVICE

(75) Inventors: Jan Andersson, Sandby (SE); Allan Dagsland, Karlshamn (SE); Hans Strid, Lomma (SE); Jan Trofast, Lund (SE); Stefan Friess, Hamburg (DE); Harald Heckenmueller, Hamburg (DE); Uwe Rollwage, Pinneberg (DE); Volker Tiedemann, Itzehoe (DE); John Conway, Sawston (GB)

(73) Assignee: Astrazeneca AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/066,319

(22) PCT Filed: Mar. 13, 1998

(86) PCT No.: PCT/SE98/00457
§ 371 (c)(1),
(2), (4) Date: May 8, 1999

(87) PCT Pub. No.: WO98/41256
PCT Pub. Date: Sep. 24, 1998

(30) Foreign Application Priority Data

Mar. 14, 1997 (SE) .................................. 9700937
Oct. 21, 1997 (SE) .................................. 9703829

(51) Int. Cl.[7] .................. A61M 15/00; A61M 16/00; B05D 7/14; B65D 83/06
(52) U.S. Cl. .................................. 128/203.15
(58) Field of Search ............... 128/203.12, 203.15, 128/203.23

(56) References Cited

U.S. PATENT DOCUMENTS

| 2,470,296 A | 5/1949 | Fields |
| 2,470,297 A | 5/1949 | Fields |
| 2,573,918 A | 11/1951 | McCuiston |

(List continued on next page.)

FOREIGN PATENT DOCUMENTS

| DE | 25 422 | 4/1983 |
| DE | 44 15 462 C1 | 8/1995 |
| EP | A 0069715 | 6/1982 |
| EP | 0 215 559 A1 | 7/1986 |
| EP | A-0237507 | 9/1987 |
| EP | 0 424 790 A2 | 5/1991 |
| EP | A-0520440 | 12/1992 |
| EP | A-0573128 | 12/1993 |
| EP | A-0703159 | 9/1994 |
| EP | A-0640354 | 3/1995 |
| EP | A-0705614 | 4/1996 |
| GB | 1 118 341 | 7/1968 |
| GB | 1 295 081 | 11/1972 |
| GB | A 1565029 | 11/1977 |
| GB | 2 179 260 A | 3/1997 |
| WO | WO 92/04066 A1 | 3/1992 |
| WO | WO 92/04068 A1 | 3/1992 |
| WO | WO 94/08552 | 4/1994 |
| WO | WO 94/11044 A2 | 5/1994 |
| WO | WO 94/13348 | 6/1994 |
| WO | WO94/14492 | 7/1994 |
| WO | WO95/03846 | * 2/1995 ............ 128/203.15 |
| WO | WO95/24234 | 9/1995 |
| WO | PCT/SE98/00457 | 3/1997 |
| WO | WO 97/30743 | 8/1997 |

Primary Examiner—Weilun Lo
Assistant Examiner—Joseph F. Weiss
(74) Attorney, Agent, or Firm—Fish & Richardson P.C.

(57) ABSTRACT

A powder inhaler for administering powder by inhalation, comprising: a flow path defined by a plurality of surfaces through which a stream of air is in use drawn on inhalation by a user; and dosing means (18) for providing a dose of powder to the flow path for entertainment in the stream of air; characterized in that the inhaler further comprises dislodging means for dislodging powder accumulated on a surface of the flow path downstream of the dosing means (18).

6 Claims, 12 Drawing Sheets

U.S. PATENT DOCUMENTS

| | | | |
|---|---|---|---|
| 3,858,583 A | | 1/1975 | Hallworth et al. |
| 3,948,264 A | | 4/1976 | Wilke et al. |
| 4,524,769 A | | 6/1985 | Wetterlin |
| 4,739,754 A | | 4/1988 | Shaner |
| 4,841,964 A | * | 6/1989 | Hurka et al. ............ 128/203.15 |
| 5,033,463 A | * | 7/1991 | Cocozza ................ 128/203.21 |
| 5,113,855 A | * | 5/1992 | Newhouse ............. 128/203.15 |
| 5,201,308 A | * | 4/1993 | Newhouse ............. 128/203.15 |
| 5,203,323 A | * | 4/1993 | Tritle .................... 128/200.23 |
| 5,331,953 A | * | 7/1994 | Andersson et al. .... 128/200.14 |
| 5,372,128 A | * | 12/1994 | Haber et al. ............ 128/203.21 |
| 5,429,122 A | * | 7/1995 | Zanen et al. ............ 128/203.15 |
| 5,437,271 A | | 8/1995 | Hodson et al. |
| 5,522,383 A | | 6/1996 | Calvert et al. |
| 5,655,523 A | * | 8/1997 | Hodson et al. ......... 128/203.15 |
| 6,082,356 A | * | 7/2000 | Stradella ................. 128/203.15 |
| 6,230,707 B1 | * | 5/2001 | Horlin ................... 128/203.15 |
| 6,257,232 B1 | * | 7/2001 | Andersson et al. ..... 128/203.15 |
| 6,325,061 B1 | * | 12/2001 | Dagsland ............... 128/203.15 |

\* cited by examiner

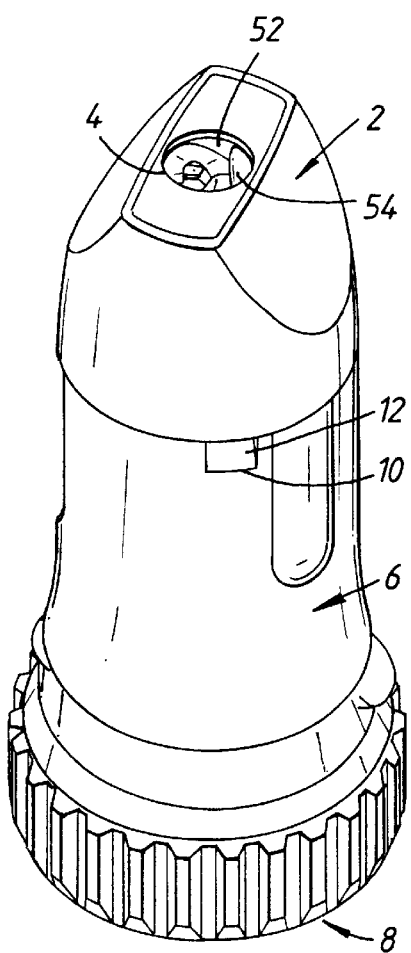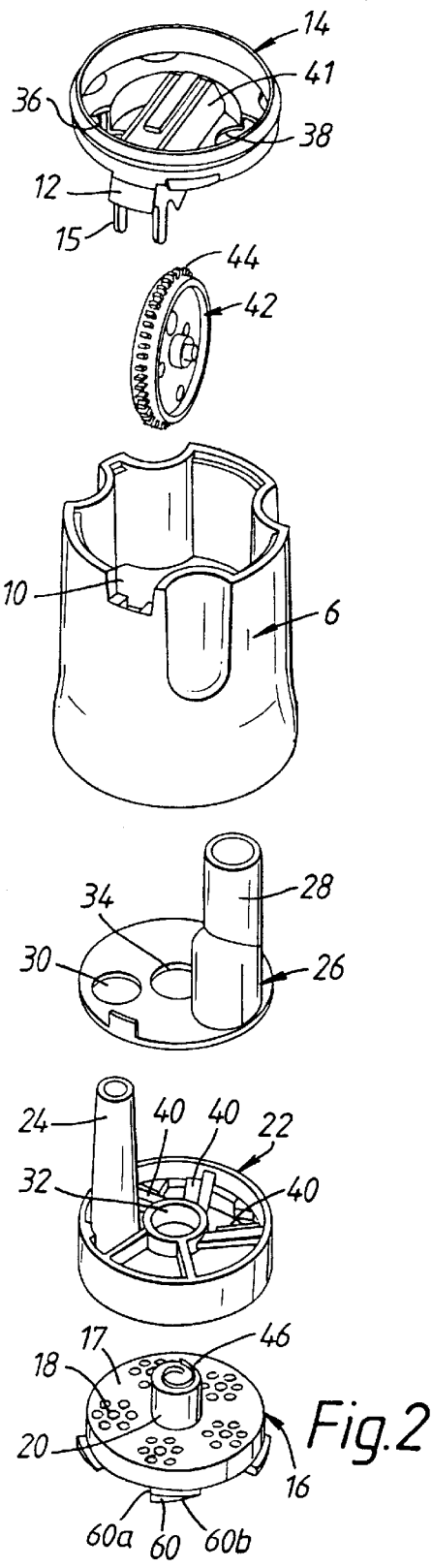
Fig.1
Fig.2

INHALATION DEVICE

The present invention relates to a powder inhaler for administering powder by inhalation.

A number of powder inhalers are known which use different systems for introducing a dose of powder into an air stream. Typically, the powder is inhaled into the lungs of a patient in order to treat, for example, asthma.

One such powder inhaler is disclosed in EP-A-0237507. This inhaler comprises an inhalation channel and a mouthpiece comprising an air chamber and an outlet nozzle, which together define a flow path through which a stream of air is drawn during inhalation by a user. This inhaler further comprises means for introducing powder into the inhalation channel. During inhalation, air is first drawn into and through the inhalation channel so as to pick up powder. The stream of air containing powder is then drawn through the air chamber and out of the outlet nozzle of the mouthpiece.

FIG. 1 illustrates such a powder inhaler. The inhaler comprises a mouthpiece 2 comprising an outlet nozzle 4, an inhaler body 6 and a rotatable grip portion 8 for operating a dosing mechanism for providing doses of powder for inhalation. The inhaler body 6 is provided with an opening 10 which is filled with a window 12 through which an indicating wheel 42 is visible so as to provide an indication as to the usage of the inhaler.

FIG. 2 illustrates in exploded view component parts disposed within and to the inhaler body 6. The inhaler body 6 is capped with a divider 14 which is fixed thereto. For aesthetic reasons the inhaler body 6 is an opaque moulding. The divider 14 is a transparent moulding which has a depending tongue 15, a part of which forms the window 12.

Within the inhaler body 6 are housed the component parts of the dosing mechanism. These component parts include a dosing unit 16 which comprises a member 17 having a planar surface in which a plurality of dosing means 18 are provided and a shaft 20 which extends axially from the centre of the member 17, an inhalation unit 22 which comprises an inhalation channel 24 and a storage unit 26 which comprises a storage chamber 28 for storing powder. The above-mentioned component parts of the dosing mechanism are assembled by passing the inhalation channel 24 through an opening 30 in the storage unit 26 and passing the shaft 20 through central openings 32, 34 in the inhalation unit 22 and the storage unit 26 respectively. When so assembled, the upper ends of the inhalation channel 24 and the storage chamber 28 pass respectively through first and second openings 36, 38 in the divider 14. In this way, the inhalation unit 22 and the storage unit 26 are fixed in position in relation to one another and the dosing unit 16 can be rotated relative thereto.

In this inhaler the storage unit 28 is open at the bottom such that in use powder is provided to the dosing unit 16 under the action of gravity and the inhalation unit 22 further comprises scrapers 40 which are resiliently biased against the surface of the member 17 in which the dosing means 18 are provided. In this way, as the dosing unit 16 is rotated, the dosing means 18, which in this inhaler comprise a plurality of through holes, are filled with powder by the scrapers 40. Powder is prevented from passing through the dosing means 18 by a plate (not illustrated) which is disposed beneath the dosing unit 16.

As illustrated in FIG. 2, the divider 14 further comprises supporting means 41 for rotatably supporting an indicating wheel 42. The indicating wheel 42 has a plurality of teeth 44 disposed around the periphery thereof which engage with a spiral groove or protrusion 46 on the end face of the shaft 20.

The supporting means 41 is configured to align the indicating wheel 42 such that a part of the periphery thereof is disposed adjacent the inner surface of the window 12. In use, as the dosing unit 16 is rotated, the spiral groove or protrusion 46 engages with one or more of the teeth 44 on the indicating wheel 42 so as to rotate the same. In this way, by providing a coloured marking on the periphery of the indicating wheel 42, it is possible to provide the user with a visible indication at the window 12 as to the usage of the inhaler.

As illustrated in FIG. 4, the mouthpiece 2 is fixed to the divider 14. The mouthpiece 2 comprises first and second parts 48, 50, the first part 48 being the part which is gripped by the lips of a user and the second part 50 being an insert fitted within the first part 48. The second part 50 comprises a tubular section 52, which includes one or more spirally or helically shaped projections 54 that act to deflect the air drawn therethrough and thereby deagglomerate any larger particles of entrained powder, and a substantially radially-directed flange 56, which provides a surface that together with upper surface of the divider 14 defines an air chamber 58 that is in fluid communication with the inhalation channel 24 through which air containing powder is drawn on inhalation by a user.

In use, as described hereinabove, powder is transferred from the storage chamber 28 to one of the dosing means 18, and, with rotation of the dosing unit 16, the one dosing means 18 provides a dose of powder to the inhalation channel 24. In this inhaler the dosing unit 16 is rotated by rotating the grip portion 8 in the counter-clockwise sense between first and second angularly-spaced positions. For this purpose the dosing unit 16 comprises wedge-shaped elements 60 disposed around the periphery of the member 17 and the grip portion 8 comprises a resilient member (not illustrated) which is configured to engage with an axially-directed surface 60a of a respective one of the wedge-shaped elements 60 so as to rotate the dosing unit 16 by pushing the respective wedge-shaped element 60. On rotation of the grip portion 8 in the opposite, clockwise, sense between the second and the first angularly-spaced positions, the dosing unit 16 remains stationary and the resilient member is located behind the axially-directed surface 60a of the adjacent wedge-shaped element 60; the resilient member riding over an inclined surface 60b of the adjacent wedge-shaped element 60.

Although the above-described known powder inhaler functions quite adequately, powder may accumulate on surfaces in the flow path through the inhaler.

It is thus an aim of the present invention to provide a powder inhaler having a construction which is such as to reduce the possibility of powder accumulating on surfaces in the flow path therethrough.

Accordingly, the present invention provides a powder inhaler for administering powder by inhalation, comprising: a flow path defined by a plurality of surfaces through which a stream of air is in use drawn on inhalation by a user; and dosing means for providing a dose of powder to the flow path for entertainment in the stream of air; characterized in that the inhaler further comprises dislodging means for dislodging powder accumulated on a surface of the flow path downstream of the dosing means.

The present invention also provides a powder inhaler for administering powder by inhalation. comprising: a housing having a screw thread; a mouthpiece attached to the housing so as to be rotatable relative thereto; and a cap for covering at least the mouthpiece, the cap having a screw thread for engaging the screw thread on the housing; characterized in that the mouthpiece and the cap are adapted such that at least a part of the mouthpiece is rotated relative to the housing on one of screwing or unscrewing the cap, which part of the mouthpiece substantially remains in fixed position relative to the housing on the other of screwing or unscrewing the cap.

By virtue of the present invention, powder which may have accumulated on inner surfaces of the inhaler is dislodged from those surfaces prior to the next inhalation. Powder is thus prevented from accumulating within the inhaler beyond a single use. In this way, any variation in the dose of powder delivered is limited to the amount of powder retained after a single use. This amount will, however, be very small and relatively insignificant.

In addition, by configuring the inhaler such that the mouthpiece is rotated automatically when the cap is removed, it is not necessary to rely upon the user to remember to rotate the mouthpiece prior to each inhalation.

The powder inhaler of the present invention may be used with any suitable form of powder, including powders introduced into the air stream in the raw state or as conglomerate, micronised or ordered mixture particles. Furthermore, the active ingredient or ingredients of the powder may be diluted with one or more substances such as lactose and may include substances for the treatment of various conditions, not necessarily respiratory conditions. Indeed, the powder can include genetic material and need not be restricted to human use only.

Medicaments suitable for administration by the powder inhaler of the present invention are any which may be delivered by inhalation and include for example β2-adrenoreceptor agonists, for example, salbutamol, terbutaline, rimiterol, fenoterol, reproterol, adrenaline. pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators, for example, ipratropium bromide and the like; glucocorticosteroids, for example, beclomethasone, fluticasone, budesonide, tipredane, dexamethasone, betamethasone, fluocinolone, triamcinolone acetonide, mometasone and the like, and their pharmacologically acceptable esters and salts; antiallergic medicaments, for example, sodium cromoglycate and nedocromil sodium; expectorants; mucolytics; antihistamines; cyclooxygenase inhibitors; leukotriene synthesis inhibitors; leukotriene antagonists; phospholipase-A2 (PLA2) inhibitors; platelet aggregating factor (PAF) antagonists and prophylactics of asthma; antiarrhythmic medicaments; tranquilisers; cardiac glycosides; hormones; antihypertensive medicaments; antidiabetic medicaments; antiparasitic medicaments; anticancer medicaments; sedatives; analgesic medicaments; antibiotics; antirheumatic medicaments; immunotherapies; antifungal medicaments; antihypotension medicaments; vaccines; antiviral medicaments; proteins; polypeptides and peptides, for example, peptide hormones and growth factors; polypeptide vaccines; enzymes; endorphines; lipoproteins and polypeptides involved in the blood coagulation cascade; vitamins; and others, for example, cell surface receptor blockers, antioxidants, free radical scavengers and organic salts of N,N'-diacetylcystine.

Preferred embodiments of the present invention will now be described hereinbelow by way of example only with reference to the accompanying drawings, in which:

FIG. 1 illustrates a perspective view of a known powder inhaler;

FIG. 2 illustrates in exploded view component parts of the inhaler of FIG. 1;

Structurally, the powder inhalers in accordance with the preferred embodiments of the present invention have many features in common with the known powder inhaler described hereinabove in relation to FIGS. 1 to 4. For this reason and in order to avoid unnecessary duplication of description, only the structural differences will be described in detail and reference is made to the preceding description of the known powder inhaler.

Figure 3:
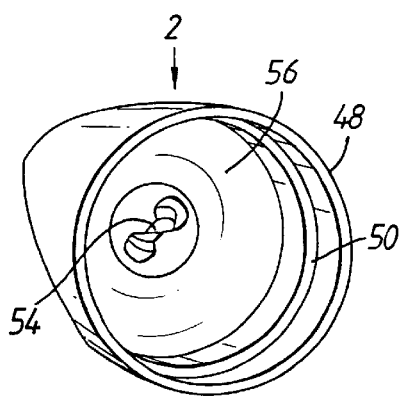
FIG. 3 illustrates the underside of the mouthpiece of the inhaler of FIG. 1.
Figure 4:
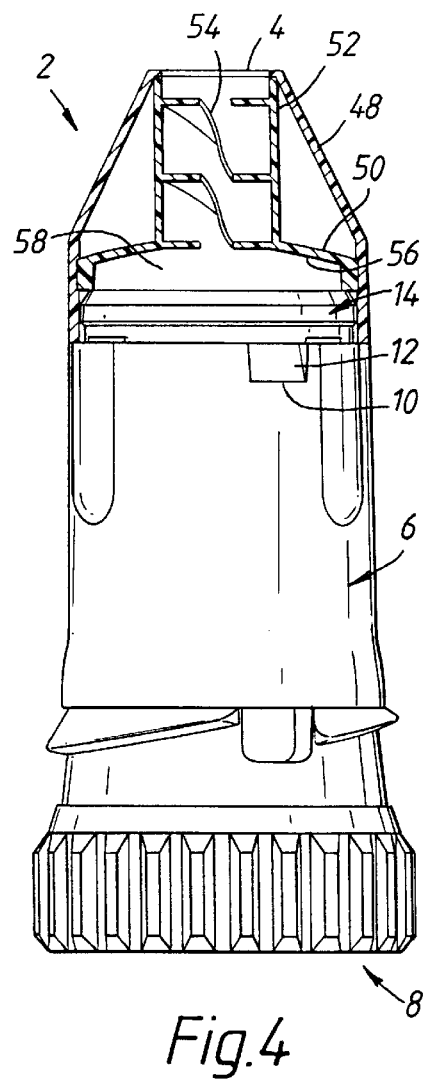
FIG. 4 illustrates a part-sectional side view of the inhaler of FIG. 1.
Figure 5:
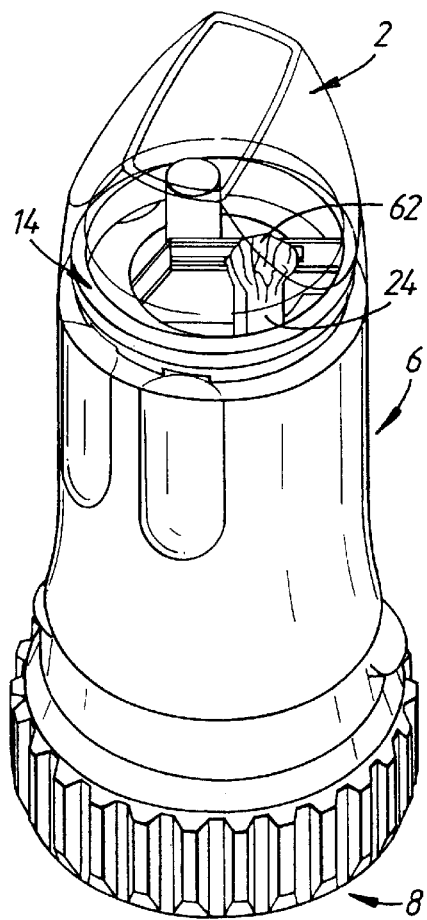
FIG. 5 illustrates a perspective view of a powder inhaler in accordance with a first embodiment of the present invention (with the mouthpiece illustrated in phantom)

FIG. 5 illustrates a powder inhaler in accordance with a first embodiment of the present invention. This embodiment is a modification of the above-described known powder inhaler. This embodiment differs from the above-described known powder inhaler in further comprising a plurality of flexible elements 62 in the form of fingers disposed around the inlet to the air chamber 58, that is, around the outlet of the inhalation channel 24. The flexible elements 62 are configured, when caused to move by a stream of air flowing through the inhaler on inhalation by a user, to contact at least a part of a surface defining the flow path. In a preferred embodiment the flexible elements 62 are of such a length as to contact the surface of the air chamber 58 defined by the second part 50 of the mouthpiece 2 during movement and thereby dislodge any powder which may have accumulated on that surface.

Figure 6A:
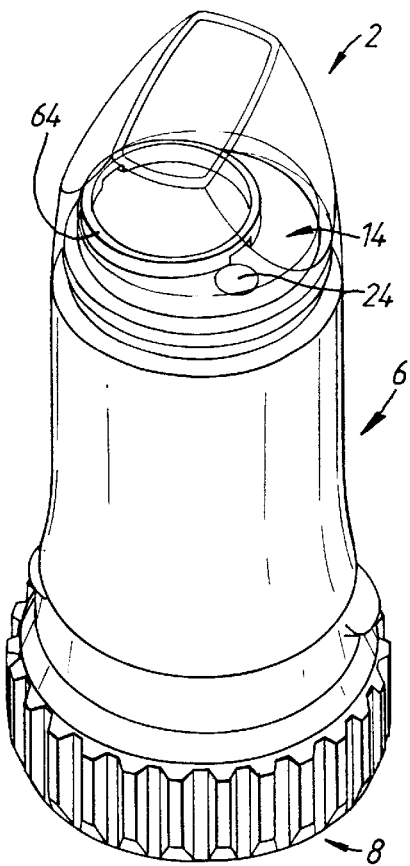
FIG. 6(a) illustrates a powder inhaler in accordance with a second embodiment of the present invention (with the mouthpiece illustrated in phantom)
Figure 6B:
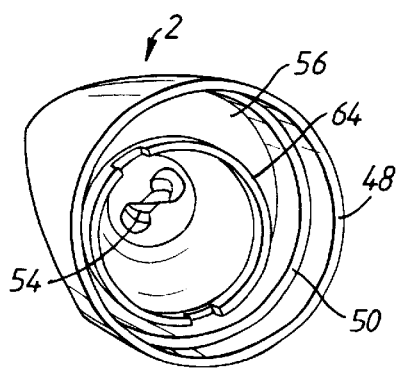
FIG. 6(b) illustrates the underside of the mouthpiece and the loose element of the inhaler of FIG. 6(a)

FIGS. 6(a) and 6(b) illustrate a powder inhaler in accordance with a second embodiment of the present invention. This embodiment is a modification of the above-described known powder inhaler. This embodiment differs from the above-described known powder inhaler in further comprising a loose element 64 which is freely movable within the air chamber 58 and in that the upper surface of the divider 14 is formed as a generally flat surface having few or no surface discontinuities. The divider 14 of this embodiment can be compared with the divider 14 of the above-described known powder inhaler whose upper surface is irregular. It will be appreciated that by forming the upper surface of the divider 14 as a generally flat surface there are fewer possible sites in which powder may accumulate and the loose element 64 cannot contact. The loose element 64 can be of any suitable shape and material. However, a ring has been identified as a particularly suitable form since this form provides a large area of contact with both the upper and lower surfaces of the air chamber 58 without impeding air flow. In use, with movement of the inhaler, the loose element 64 is moved within the air chamber 58 and thereby any powder which may have accumulated on inner surfaces thereof is dislodged. In a preferred embodiment the loose element 64 is formed of a relatively dense material, for example a metal, such that impact of the loose element 64 against inner surfaces of the air chamber 58 induces vibrations in the inhaler, in particular in the second part 50 of the mouthpiece 2, which additionally act to dislodge any powder which may have accumulated on surfaces of the flow path.

Figure 7:
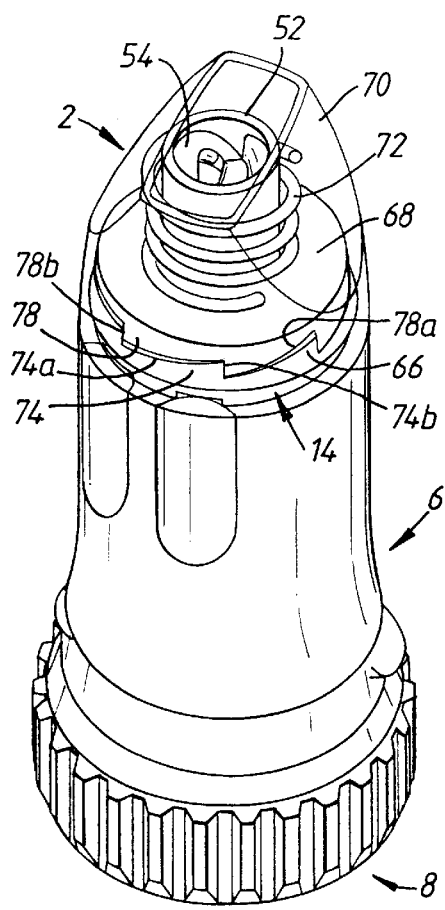
FIG. 7 illustrates a powder inhaler in accordance with a third embodiment of the present invention (with part of the mouthpiece illustrated in phantom)

FIG. 7 illustrates a powder inhaler in accordance with a third embodiment of the present invention. This embodiment is a modification of the above-described known powder inhaler. This embodiment differs from the above-described known powder inhaler in that the mouthpiece 2 comprises first, second and third parts 66, 68, 70 and a biasing means 72, preferably a compression spring, for axially biasing the first and second parts 66, 68 towards one another. The first part 66, similarly to the second part 50 of the mouthpiece 2 of the above-described known powder inhaler, comprises a tubular section 52, which includes one or more spirally or helically shaped projections 54 that act to deflect the air drawn therethrough and thereby deagglomerate any larger particles of entrained powder, and a substantially radially-directed flange 56, the lower surface of which together with upper surface of the divider 14 defines an air chamber 58 that is in fluid communication with the inhalation channel 24 through which air containing powder is drawn on inhalation by a user. The first part 66 differs from the second part 50 of the above-described known powder inhaler in that the upper surface of the flange 56 is provided with a plurality of axially-directed projections 74, in this embodiment of triangular cross-section, each with a first flank 74a which faces in one sense, in this embodiment in the clockwise sense when viewed from above, and a second flank 74b which faces in the opposite sense, in this embodiment in the counter-clockwise sense when viewed from above. In this embodiment the projections 74 are disposed about the periphery of the flange 56. In another embodiment the projections 74 can each be formed as a radial sector. The second part 68 is rotatable relative to the first part 66 and is rotatably fixed in relation to the third part 70. The second part 68 comprises a plate of substantially the same radial dimension as the flange 56 of the first part 66. The lower surface of the second part 68 is provided with a plurality of axially-directed projections 78, the cross-section of which in this embodiment is complimentary to the projections 74 on the flange 56 of the first part 66. In this embodiment the projections 78 are of triangular cross-section, each with a first flank 78a which faces in one sense, in this embodiment in the counter-clockwise sense when viewed from above, and a second flank 78b which faces in the opposite sense, in this embodiment in the clockwise sense when viewed from above. In this embodiment the projections 78 are disposed about the periphery of the second part 68. In another embodiment the projections 78 can each be formed as a radial sector. The third part 70, similarly to the first part 48 of the mouthpiece 2 of the above-described known powder inhaler, is clipped to the divider 14 and is the part which is gripped by the lips of a user. In use, on rotation of the third part 70, the second part 68 which is rotated concomitantly therewith is axially displaced away from the first part 66 as the first flanks 78a of the projections 78 on the second part 68 ride along the respective first flanks 74a of the projections 74 on the flange 56 of the first part 66. With continued rotation of the third part 70, the second part 68 is further axially displaced away from the flange 56 of the first part 66 until the point is reached where the trailing edges of the first flanks 78a of the projections 78 on the second part 68 pass beyond the leading edges of the first flanks 74a of the respective projections 74 on the flange 56 of the first part 66. At that point, the second part 68 is rapidly driven axially under the action of the biasing means 72 into contact with the flange 56 of the first part 66. This sharp contact between the projections 78 on the second part 68 and the projections 74 on the flange 56 of the first part 66 which is achieved by the rapid movement induces vibrations in the inhaler, in particular in the first part 66, and thereby dislodges powder which may have accumulated on the lower surface of the flange 56 that defines the upper surface of the air chamber 58. It will be appreciated that whilst this preferred embodiment incorporates axially-directed projections 74, 78 of triangular cross-section, other cross-sections which would achieve the effect of inducing vibrations in the inhaler, particularly in the first part 66, could also be equally used.

Figure 8:
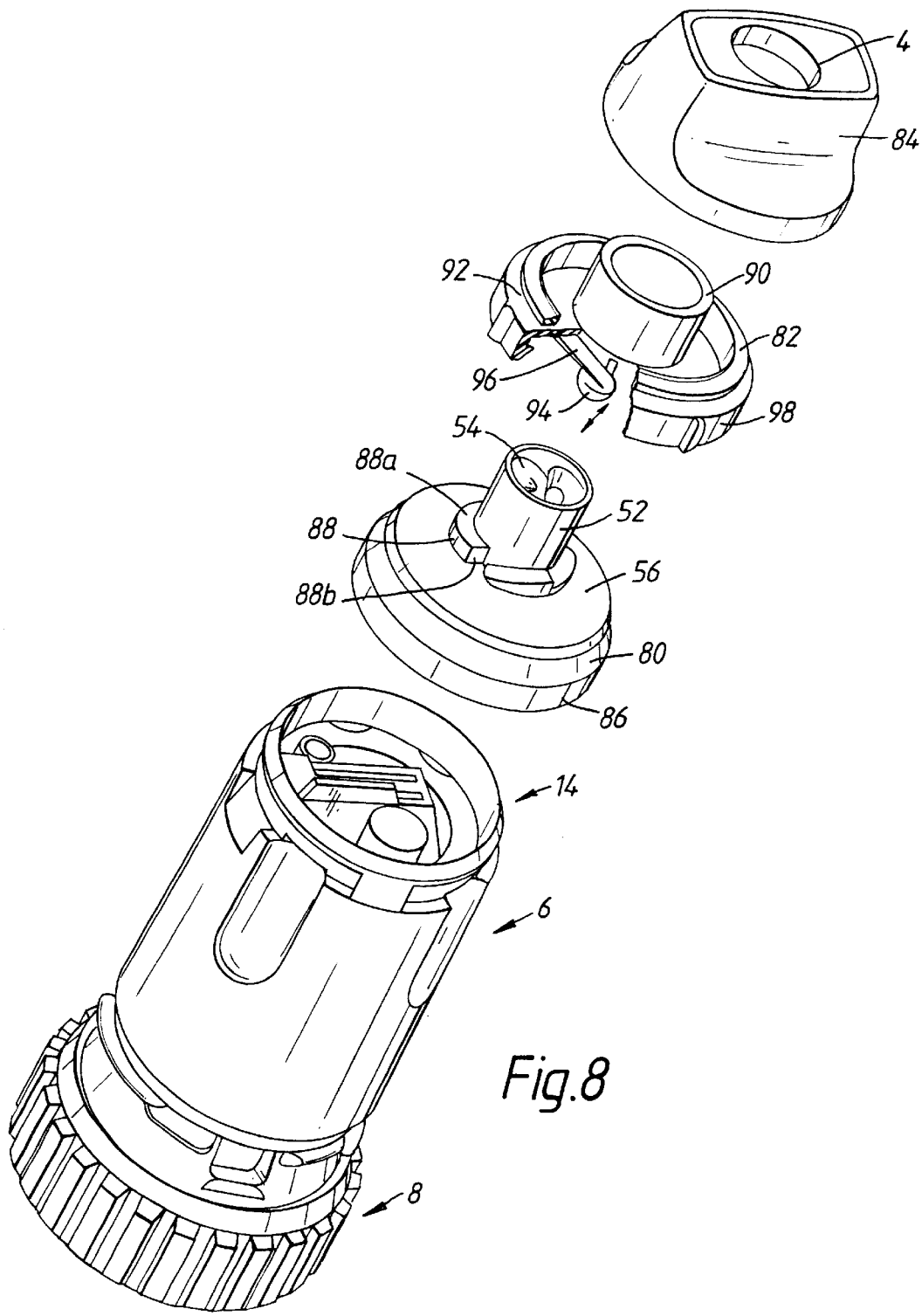
FIG. 8 illustrates in exploded view a powder inhaler in accordance with a fourth embodiment of the present invention.

FIG. 8 illustrates a powder inhaler in accordance with a fourth embodiment of the present invention. This embodiment is a modification of the above-described known powder inhaler. This embodiment differs from the above-described known powder inhaler in that the mouthpiece 2 comprises first, second and third parts 80, 82, 84. The first part 80, similarly to the second part 50 of the mouthpiece 2 of the above-described known powder inhaler, comprises a tubular section 52, which includes one or more spirally or helically shaped projections 54 that act to deflect the air drawn therethrough and thereby deagglomerate any larger particles of entrained powder, and a substantially radially-directed flange 56, which provides a surface that together with upper surface of the divider 14 defines an air chamber 58 that is in fluid communication with the inhalation channel 24 through which air containing powder is drawn on inhalation by a user. The first part 80 differs from the second part 50 of the above-described known powder inhaler in further comprising a downwardly-directed extension 86 disposed about the periphery of the flange 56 by which the first part 80 is clipped to the divider 14 and a plurality of axially-directed projections 88 on the upper surface of the flange 56, each in this embodiment of triangular cross-section. disposed about the outer periphery of the tubular section 52. In this embodiment each of the projections 88 comprises a first flank 88a which faces in one sense, in this embodiment in the clockwise sense when viewed from above, and a second flank 88b which faces in the opposite sense, in this embodiment in the counter-clockwise sense when viewed from above. The second part 82 comprises a tubular section 90 which is located over the tubular section 52 of the first part 80, a flange 92 which extends radially from the tubular section 90 and an element 94 which is connected to the flange 92 by a resilient arm 96 and is configured to ride over the projections 88. The flange 92 includes a downwardly-directed peripheral extension 98 by which the second part 82 is clipped to the first part 80 so that the flanges 56. 92 have a fixed axial relationship. The second part 82 is fitted to the first part 80 so as to be rotatable in one sense relative thereto, in this embodiment in the counter-clockwise sense when viewed from above. The third part 84, similarly to the first part 48 of the mouthpiece 2 of the above-described known powder inhaler, is the part which is gripped by the lips of a user. In this embodiment the third part 84 is fixed to the second part 82 such that the second part 82 rotates concomitantly therewith. In this way, on rotation of the third part 84 in one sense, in this embodiment in the counter-clockwise sense when viewed from above. the element 94 rides along the first flank 88a of one of the projections 88 and is displaced axially away from the flange 56 of the first part 80. As the element 94 is displaced the resilient arm 96 is progressively deflected. The element 94 is further axially displaced until the element 94 passes beyond the leading edge of the first flank 88a of the respective projection 88. At that point, the element 94 is rapidly driven under the action of the loaded arm 96 into contact with the flange 56 of the first part 80. This sharp contact between the element 94 and the flange 56 of the first part 80 which is achieved by the rapid movement induces vibrations in the inhaler, in particular in the first part 80, and thereby dislodges powder which may have accumulated on the lower surface of the flange 56 which defines the upper surface of the air chamber 58.

Figure 9:
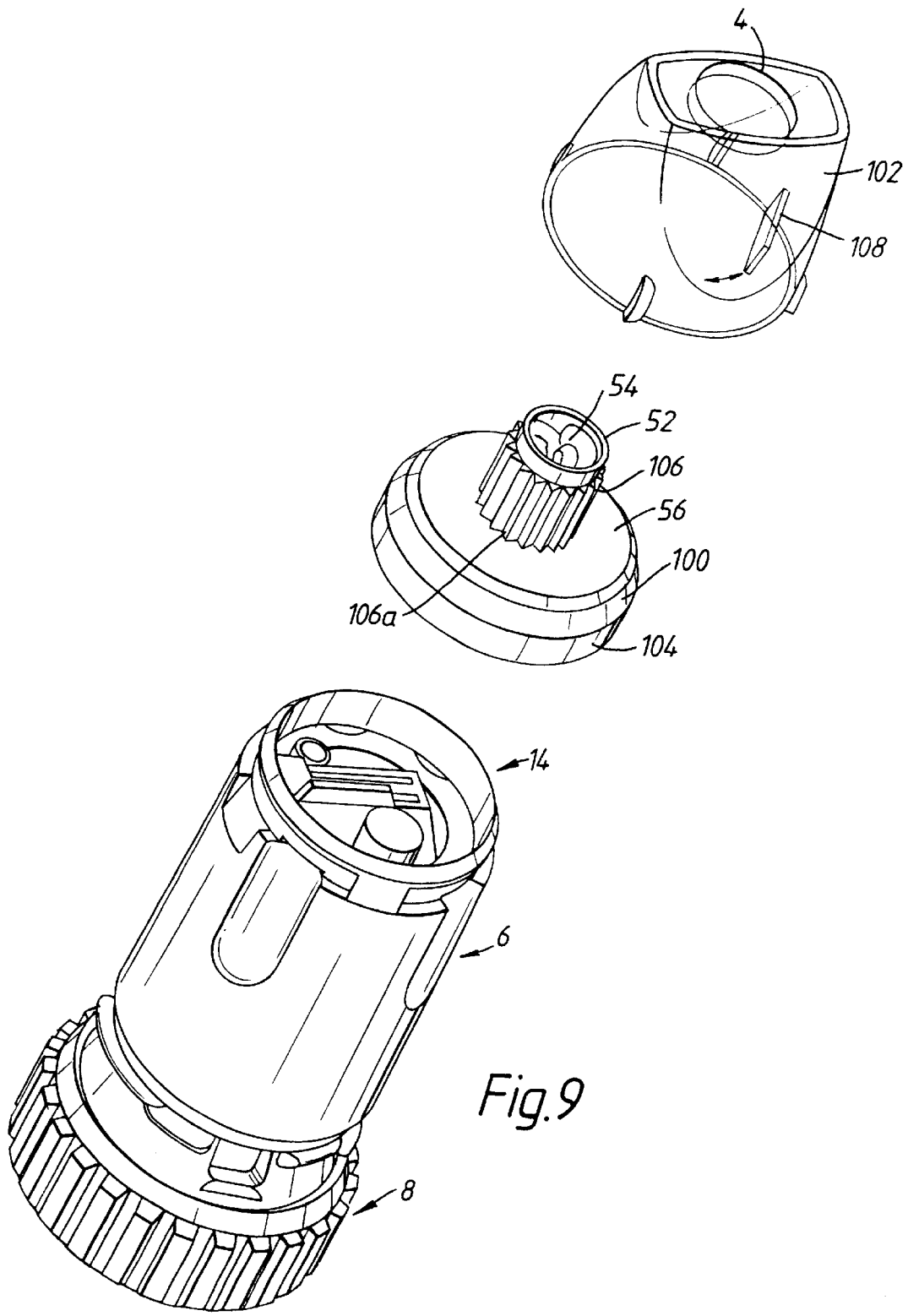
FIG. 9 illustrates in exploded view a powder inhaler in accordance with a fifth embodiment of the present invention.

FIG. 9 illustrates a powder inhaler in accordance with a fifth embodiment of the present invention. This embodiment is a modification of the above-described known powder inhaler. In this embodiment the mouthpiece 2 comprises first and second parts 100, 102. The first part 100, similarly to the second part 50 of the mouthpiece 2 of the above-described known powder inhaler, comprises a tubular section 52, which includes one or more spirally or helically shaped projections 54 that act to deflect the air drawn therethrough and thereby deagglomerate any larger particles of entrained powder, and a substantially radially-directed flange 56, which provides a surface that together with upper surface of the divider 14 defines an air chamber 58 that is in fluid communication with the inhalation channel 24 through which air containing powder is drawn on inhalation by a user. The first part 100 differs from the second part 50 of the above-described known powder inhaler in further comprising a downwardly-directed extension 104 disposed about the periphery of the flange 56 by which the first part 100 is clipped to the divider 14 and a plurality of radially-directed projections 106, each in this embodiment of triangular cross-section, disposed about the outer periphery of the tubular section 52. The second part 102, similarly to the first part 48 of the mouthpiece 2 of the above-described known powder inhaler, is the part which is gripped by the lips of a user. In this embodiment the second part 102 comprises an inwardly-directed member 108, the distal end of which is configured to engage the projections 106 disposed about tubular section 52. In this way, on rotation of the second part 102 relative to the first part 100, in this embodiment in the counter-clockwise sense when viewed from above, the member 108 is deflected radially outwardly on riding over a first flank 106a of one of the projections 106. The member 108 is progressively deflected until passing beyond the leading edge of the first flank 106a of the respective projection 106. At that point, the distal end of the member 108 which is under load is rapidly driven radially inwardly into contact with the first flank 106a of the adjacent projection 106. This sharp contact between the distal end of the member 108 and the tubular section 52 induces vibrations in the inhaler, in particular in the first part 100, and thereby dislodges powder which may have accumulated on the lower surface of the flange 56 which defines the upper surface of the air chamber 58. In this embodiment the member 108 is formed of a resilient material. It will be appreciated, however, that the member 108 could be formed of a rigid material and biased against the tubular section 52 by a biasing means such as a spring.

Figure 10:
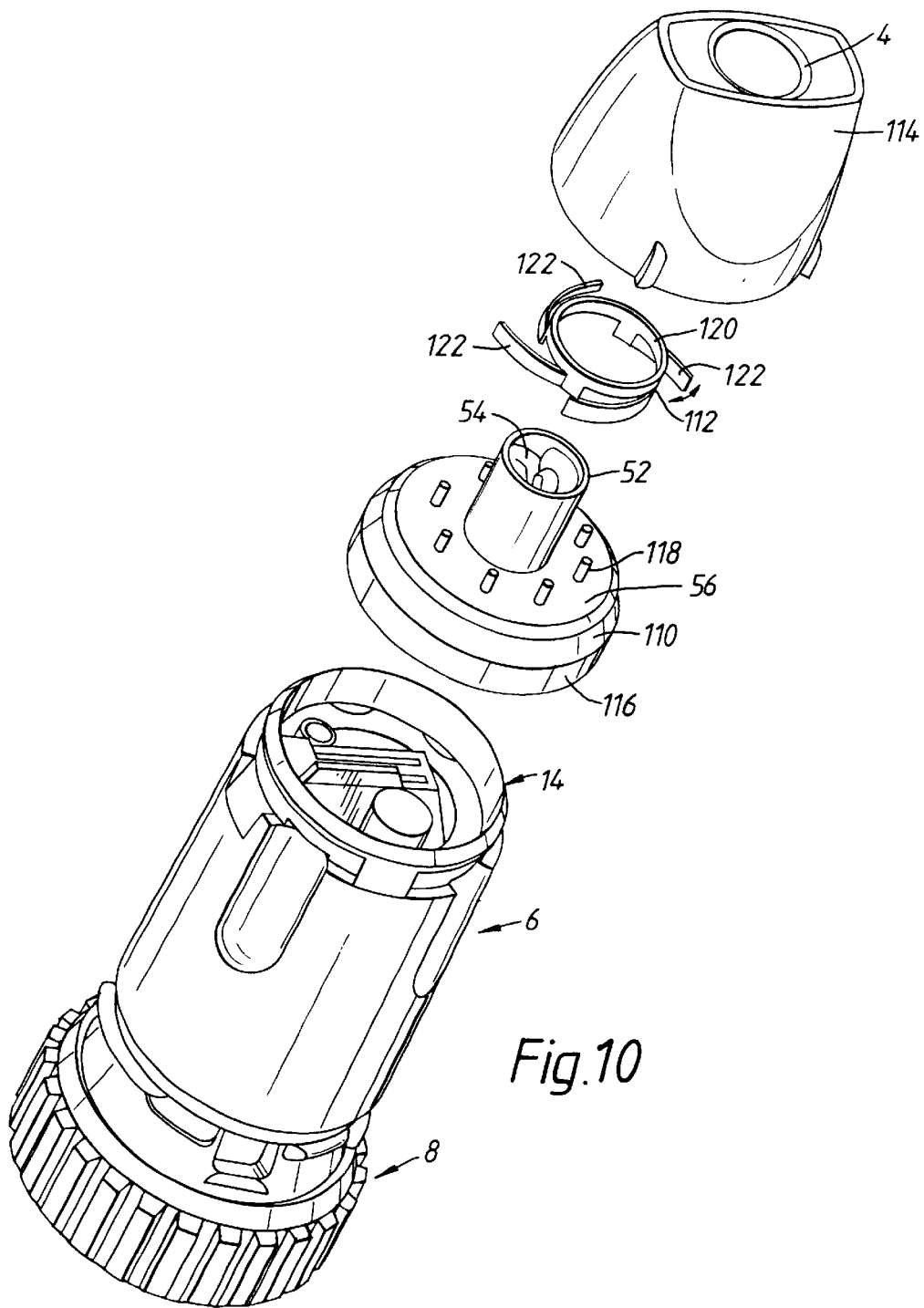
FIG. 10 illustrates in exploded view a powder inhaler in accordance with a sixth embodiment of the present invention.

FIG. 10 illustrates a powder inhaler in accordance with a sixth embodiment of the present invention. This embodiment is a modification of the above-described known powder inhaler. This embodiment differs from the above-described known powder inhaler in that the mouthpiece 2 comprises first, second and third parts 110, 112, 114. The first part 110, is similarly to the second part 50 of the mouthpiece 2 of the above-described known powder inhaler, comprises a tubular section 52, which includes one or more spirally or helically shaped projections 54 that act to deflect the air drawn therethrough and thereby deagglomerate any larger particles of entrained powder, and a substantially radially-directed flange 56, which provides a surface that together with upper surface of the divider 14 defines an air chamber 58 that is in fluid communication with the inhalation channel 24 through which air containing powder is drawn on inhalation by a user. The first part 110 differs from the second part 50 of the above-described known powder inhaler in further comprising a downwardly-directed extension 116 disposed about the periphery of the flange 56 by which the first part 110 is clipped to the divider 14 and a plurality of upwardly-directed axial projections 118, each in this embodiment in the form of a stub of circular cross-section, disposed at a distance about the outer periphery of the tubular section 52. In this embodiment the projections 118 are equi-spaced on a circle about the tubular section 52. The second part 112 comprises a tubular section 120 which is located over the tubular section 52 of the first part 110 and a plurality of members 122 which extend at least in part radially outwardly from the tubular section 120. The third part 114, similarly to the first part 48 of the mouthpiece 2 of the above-described known powder inhaler, is the part which is gripped by the lips of a user. In this embodiment the second part 112 is fixed to the third part 114 so as to rotate concomitantly therewith and the third part 114 is clipped to the first part 110 so as to be rotatable relative thereto. In this way, on rotation of the third part 114 in one sense, in this embodiment in the counter-clockwise sense when viewed from above, the members 122 each ride over a respective one of the projections 118 and are deflected radially inwardly. With continued rotation, the elements 122 are progressively deflected and thereby biased until the distal ends thereof pass beyond the respective projections 118. At that point, the distal ends of the members 122 are rapidly driven radially outwardly and contact each of the respective adjacent projections 118. This sharp contact between the members 122 and the projections 118 which is achieved by the rapid movement induces vibrations in the inhaler. in particular in the first part 110, and thereby dislodges powder which may have accumulated on the lower surface of the flange 56 which defines the upper surface of the air chamber 58.

Figure 11:
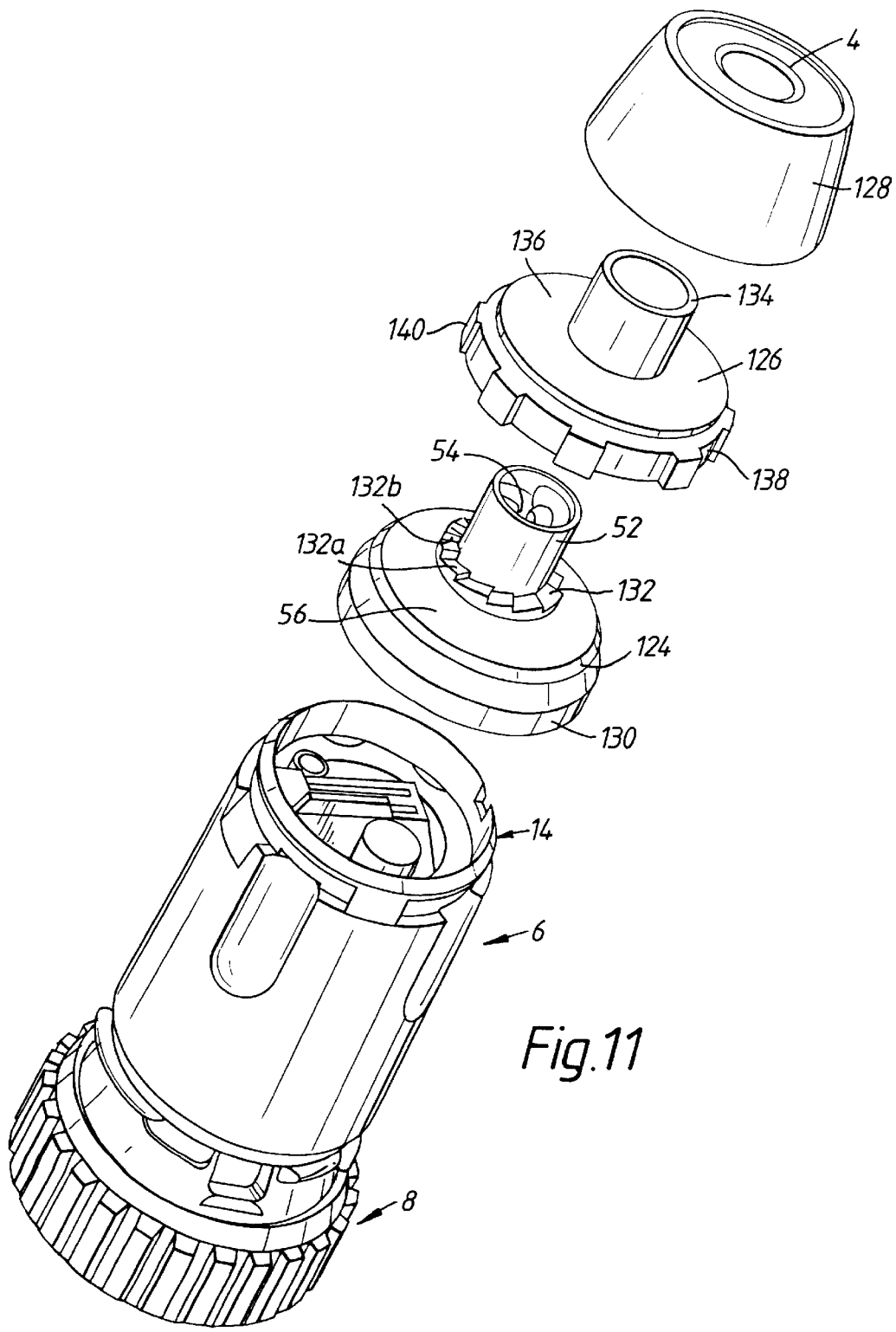
FIG. 11 illustrates in exploded view a powder inhaler in accordance with a seventh embodiment of the present invention.

FIG. 11 illustrates a powder inhaler in accordance with a seventh embodiment of the present invention. This embodiment is a modification of the above-described known powder inhaler. This embodiment differs from the above-described known powder inhaler in that the mouthpiece 2 comprises first, second and third parts 124, 126, 128. The first part 124, similarly to the second part 50 of the mouthpiece 2 of the above-described known powder inhaler, comprises a tubular section 52, which includes one or more spirally or helically shaped projections 54 that act to deflect the air drawn therethrough and thereby deagglomerate any larger particles of entrained powder, and a substantially radially-directed flange 56, which provides a surface that together with upper surface of the divider 14 defines an air chamber 58 that is in fluid communication with the inhalation channel 24 through which air containing powder is drawn on inhalation by a user. The first part 124 differs from the second part 50 of the above-described known powder inhaler in further comprising a downwardly-directed extension 130 disposed about the periphery of the flange 56 by which the first part 124 is clipped to the divider 14 and a plurality of axially-directed projections 132, each in this embodiment of triangular cross-section, disposed about the outer periphery of the tubular section 52. In this embodiment each of the projections 132 comprises a first flank 132a which faces in one sense, in this embodiment in the clockwise sense when viewed from above, and a second flank 132b which faces in the opposite sense, in this embodiment in the counter-clockwise sense when viewed from above. The first part 124 further differs from the second part 50 of the above-described known powder inhaler in that at least a part of the flange 56 is formed of a resilient material such that the tubular section 52 can be moved axially relative to the peripheral extension 130 and thereby resiliently deform the flange 56. In a preferred embodiment the flange 56 is formed of sufficiently small thickness in order to exhibit the necessary resiliency to allow for deformation. In this embodiment the second part 126 comprises a tubular section 134 which is located over the tubular section 52 of the first part 124, a flange 136 which extends radially from the tubular section 134 and a downwardly-directed extension 138 disposed about the periphery of the flange 136 by which the second part 126 is clipped to the first part 124 so as to be rotatable thereto. In this embodiment the outer periphery of the extension 138 is provided with a plurality of radially-directed projections 140 which act as a grip for a user. The second part 126 further comprises a plurality of axially-directed projections (not illustrated) disposed to the lower surface of the flange 136, the cross-section of which projections is in this embodiment complimentary to the projections 132 disposed about the periphery of the tubular section 52 of the first part 66. In this embodiment the projections on the lower surface of the flange 136 are of triangular cross-section, each with a first flank which faces in one sense, in this embodiment in the counter-clockwise sense when viewed from above, and a second flank which faces in the opposite sense, in this embodiment in the clockwise sense when viewed form above. The second part 126 is fitted to the first part 124 so as to be rotatable in one sense relative thereto, in this embodiment in the counter-clockwise sense when viewed from above. The third part 128. similarly to the first part 48 of the mouthpiece 2 of the above-described known powder inhaler, is the part which is gripped by the lips of a user. In this embodiment the third part 128 is fixed to the second part 126 so as to rotate concomitantly therewith. In this way, on rotation of one of the second part 126 or the third part 128 in one sense, in this embodiment in the counter-clockwise sense when viewed from above, the tubular section 52 is displaced downwardly axially relative to the extension 130 as the first flanks of the projections on the lower surface of the flange 136 ride along the first flanks 132a of the respective projections 132 on the tubular section 52. The tubular section 52 is further axially displaced until the trailing edges of the first flanks of the projections on the lower surface of the flange 136 pass beyond the leading edges of the first flanks 132a of the respective projections 132 on the tubular section 52. At that point, the tubular section 52 is returned rapidly to the original axial position and the projections 132 on the tubular section 52 contact the projections on the lower surface of the flange 136. This sharp contact between the projections 132 on the tubular section 52 and the projections on the lower surface of the flange 136 which is achieved by the rapid movement induces vibrations in the inhaler, in particular in the first part 124, and thereby dislodges powder which may have accumulated on the lower surface of the flange 56 which defines the upper surface of the air chamber 58.

Figure 12:
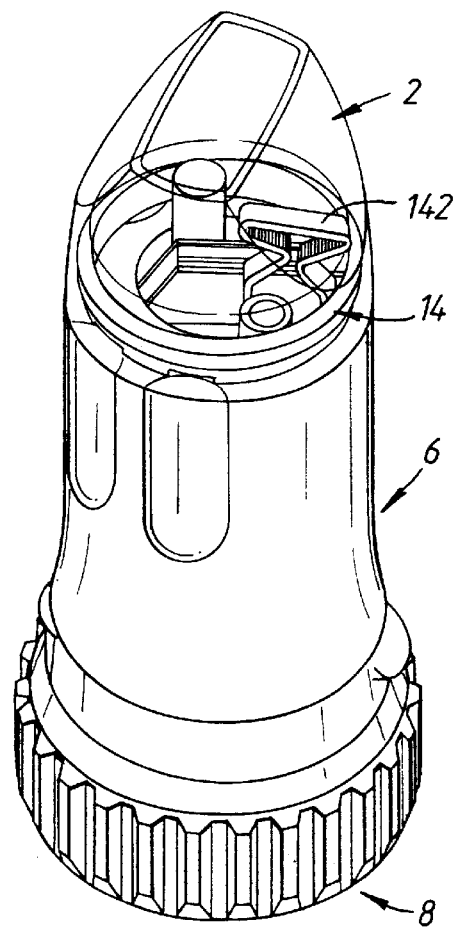
FIG. 12 illustrates a perspective view of a powder inhaler in accordance with an eighth embodiment of the present invention (with the mouthpiece illustrated in phantom)

FIG. 12 illustrates a powder inhaler in accordance with an eighth embodiment of the present invention. This embodiment is a modification of the above-described known powder inhaler. This embodiment differs from the above-described known powder inhaler in further comprising a member 142 disposed to the upper surface of the divider 14 which contacts the lower surface of the second part 50 of the mouthpiece 2 defining a part of the air chamber 58. In preferred embodiments the member 142 comprises a scraper or a brush. In this embodiment,the mouthpiece 2 is rotatable relative to the inhaler body 6. In use, on rotating the second part 50 relative to the member 142, in this embodiment by rotating the mouthpiece 2, the member 142 acts to dislodge powder which may have accumulated on the lower surface of the second part 50. In a preferred embodiment, where the top of the storage chamber 28 includes an inlet which is closed by a separate plug, the member 142 can be formed as an integral part of the plug or be attached to the plug. It will be appreciated that whilst in this embodiment the member 142 is configured to contact the lower surface of the second part 50 which defines an upper surface of the air chamber 58, in an alternative embodiment the member 142 could instead be configured to contact the upper surface of the divider 14 which defines the lower surface of the air chamber 58. In another embodiment one or more members 142 could be provided which are configured to contact both the lower surface of the second part 50 and the upper surface of the divider 14.

Figure 13:
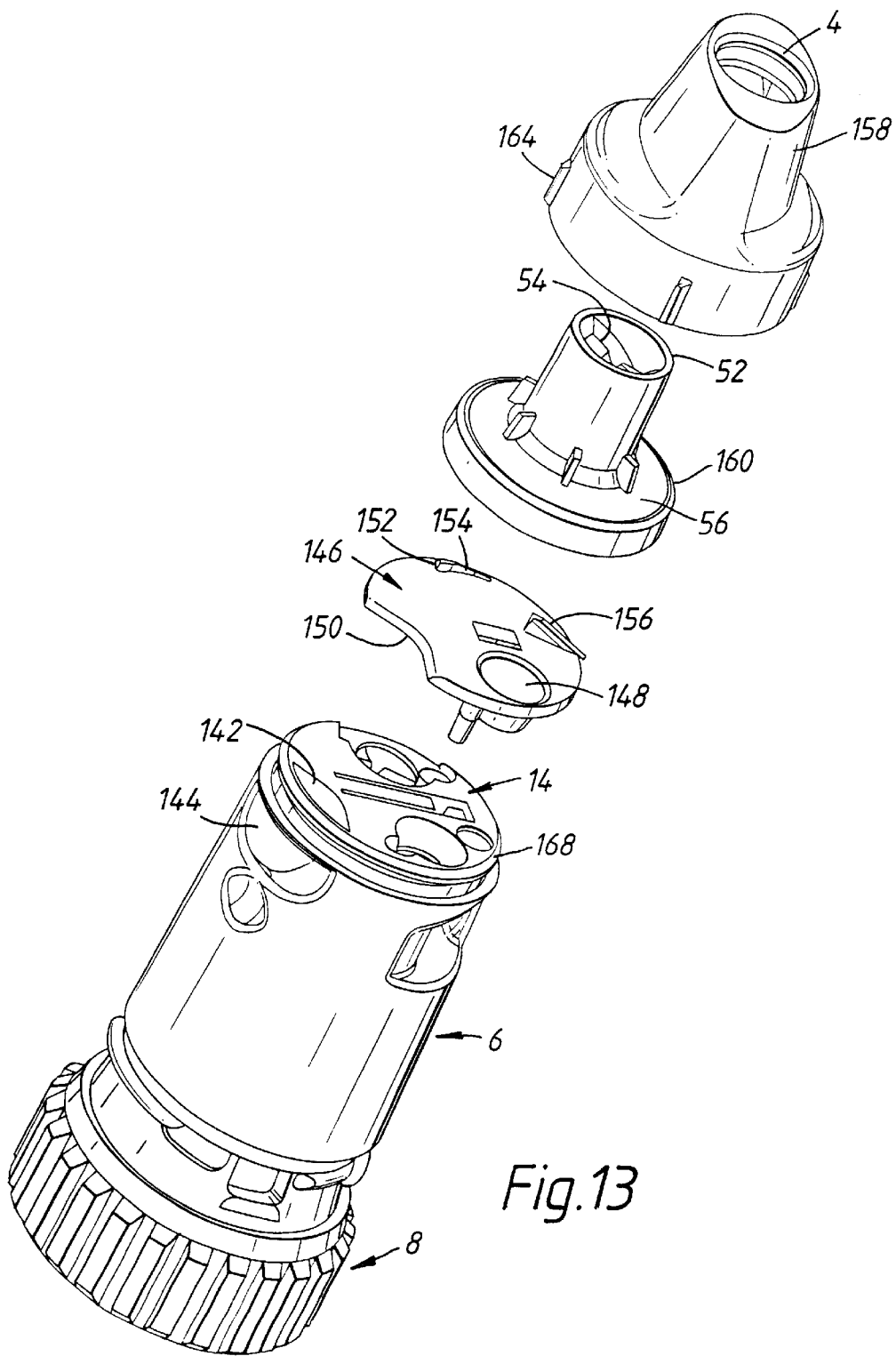
FIG. 13 illustrates in exploded view a powder inhaler in accordance with a ninth embodiment of the present invention.
Figure 14:
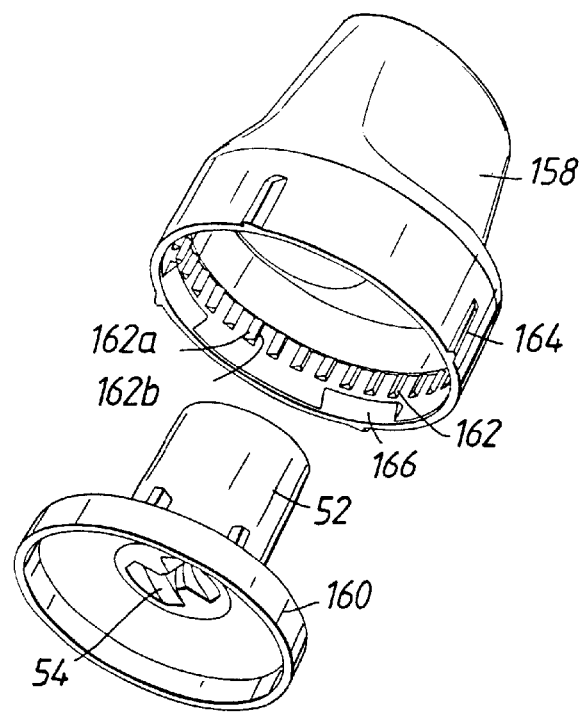
FIG. 14 illustrates in exploded view the component parts of the mouthpiece of the inhaler of FIG. 13.
Figure 15:
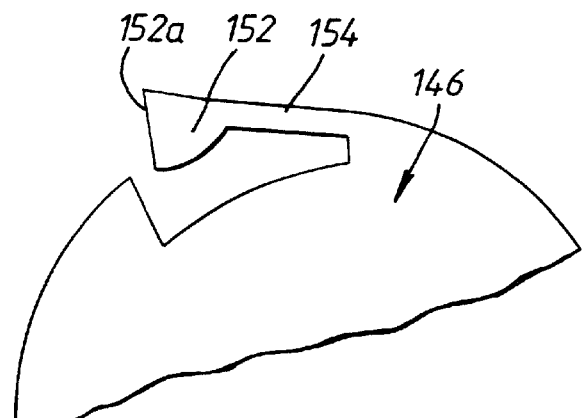
FIG. 15 illustrates a plan view of part of the cover plate of the inhaler of FIG. 13.
Figure 16:
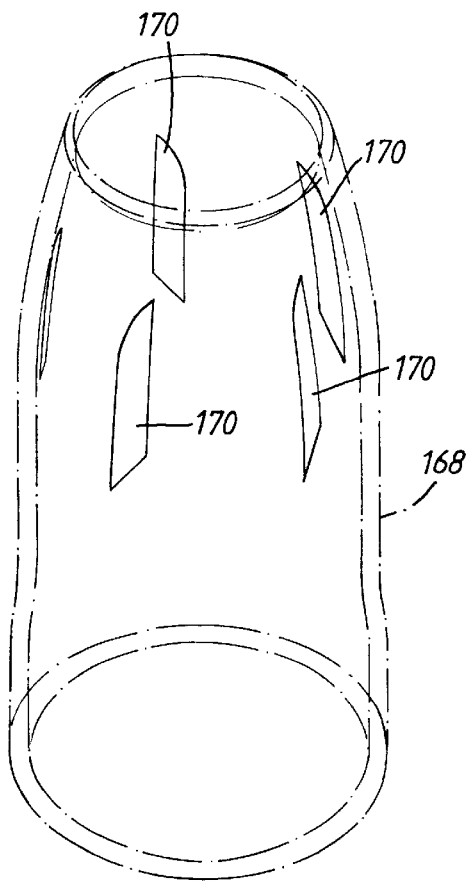
FIG. 16 illustrates the cap for the inhaler of FIG. 13.

FIG. 13 illustrates a powder inhaler in accordance with a ninth embodiment of the present invention. This embodiment is a modification of the above-described known powder inhaler. This embodiment differs from the above-described known powder inhaler in that the divider 14 further comprises a supplementary air inlet 142 which is in fluid communication with an opening 144 in the peripheral wall of the inhaler body 6 and in further comprising a cover plate 146 which is located above the divider 14. The cover plate 146 comprises first and second openings 148, 150 which correspond respectively to the inhalation channel 24 and the supplementary air inlet 142. The cover plate 146 further comprises an outwardly-biased element 152 which is connected to the main body thereof by a resilient arm 154. In this embodiment the element 152 has an end face 152a which is substantially radially directed. The cover plate 146 still further comprises a member 156 which is configured to contact a part of the lower surface of the flange 56 defining the upper surface of the air chamber 58. In preferred embodiments the member 156 comprises one of a scraper or a brush. In this embodiment the member 156 is integrally formed with the cover plate 146 and comprises an arm which is formed of resilient material and acts as a scraper. In this embodiment the mouthpiece 2 comprises first and second parts 158, 160. This embodiment further differs from the above-described known powder inhaler in that the first part 158 further comprises a plurality of radially inwardly-directed projections 162 and a plurality of radially outwardly-directed projections 164. Each of the projections 162 comprises a first flank 162a which faces in one sense, in this embodiment in the counter-clockwise sense when viewed from above, and a second flank 162b which faces in the other sense, in this embodiment in the clockwise sense when viewed form above. In this embodiment the second flanks 162b of the projections 162 are substantially radially directed. In this way, the inhaler is configured such that the mouthpiece 2 cannot be freely rotated relative to the inhaler body 6, which would be undesirable when a user was trying to grip the mouthpiece 2 in the lips. In this embodiment the mouthpiece 2 is attached to the inhaler body 6 by means of clips 166 which engage a ridge 168 that is formed about the periphery of the divider 14. In this embodiment the inhaler is configured so as to allow the mouthpiece 2 to be rotated in the counter-clockwise sense on the application of a relatively small force, but to provide significant resistance to rotation of the mouthpiece 2 in the clockwise sense and thereby permit only forced rotation in that sense. On rotating the mouthpiece 2 in the counter-clockwise sense the element 152 rides over the first flanks 162a of the projections 162 on the application of a relatively low force, with the resilient arm 154 being deflected radially inwardly. On rotating the mouthpiece 2 in the clockwise sense the end face 152a of the element 152 abuts the second flank 162b of one of the projections 162, which end face 152a and second flanks 162b of the projections 162 are formed so as to provide surfaces at a small angle relative to the radial direction. In order to rotate the element 152 beyond the respective projection 162, a relatively high force has to be applied to overcome the resistance between the end face 152a of the element 152 the second flank 162b of the respective projection 162. Whilst the inhaler could be configured to prevent the mouthpiece 2 being rotated in one sense by providing the end face 152a of the element 152 and the second flanks 162b of the projections 162 as radially-directed surfaces, in this embodiment it has been recognized that a user could attempt to force the mouthpiece 2 to rotate in that sense which may lead to damage being caused such as by deforming any of the element 152, the resilient arm 154 or the projections 162. In use, on rotating the mouthpiece 2 relative to the inhaler body 6, the lower surface of the flange 56 of the second part 160 is rotated relative to the member 156 thereby causing powder which may have accumulated on that part of the lower surface of the flange 56 immediately upstream of the member 156 in a rotational sense to be removed.

In a preferred embodiment the inhaler further comprises a cap 168 which is adapted to rotate the mouthpiece 2 on removal. In this embodiment the cap 168 includes a plurality of resilient members 170 disposed about the inner periphery thereof which engage with the outwardly-directed projections 164 on the first part 158 of the mouthpiece 2. The members 170 extend axially and enclose an acute angle with the inner periphery of the cap 168; the distal ends of the members 170 being directed in the counter-clockwise sense when viewed from above. By having an axial length the members 170 engage the outwardly-directed projections 164 on the first part 158 for the entire period that the cap 168 is removed, in this embodiment by unscrewing in the counter-clockwise sense when viewed from above. In use, when the cap 168 is removed, one or more of the members 170 engage respective projections 164 on the first part 158 and cause the mouthpiece 2 to be rotated relative to the inhaler body 6, thereby causing the member 156 to remove powder which may have accumulated on that part of the lower surface of the flange 56 upstream, in a rotational sense, of the member 156. In this way, whenever a user removes the cap 168 the mouthpiece 2 is automatically rotated. Further, the mouthpiece 2 is rotated in only one direction and only when the cap 168 is removed. This arrangement has a number of advantages. Specifically, in that powder is dislodged immediately prior to inhalation. In addition, on removing the cap 168, the grip portion 8 is tended to be rotated in the sense opposite to that required to provide a dose of powder to the inhalation channel 24. Thus, there is no risk of a user loading the inhaler on removing the cap 168. In fitting the cap 168, in this embodiment by screwing in the clockwise sense, the members 170 are deflected and ride over the respective projections 164 on the first part 158. In a preferred embodiment the cap 168 is provided with a greater number of members 170 than the first part 158 is provided with projections 164. In this way, the angle through which the cap 168 has to be rotated before engaging one or more of the projections 164 is minimized. In addition, when the cap 168 is fitted, the members 170 pass over the projections 164 one at a time, such that with the cap 168 fitted no more than one member 170 can be left in a deformed state; extended periods of deformation being undesirable in causing relaxation of the material of the members 170. In a preferred embodiment the cap 168 and the members 170 are formed as an integral moulding.

Figure 17:
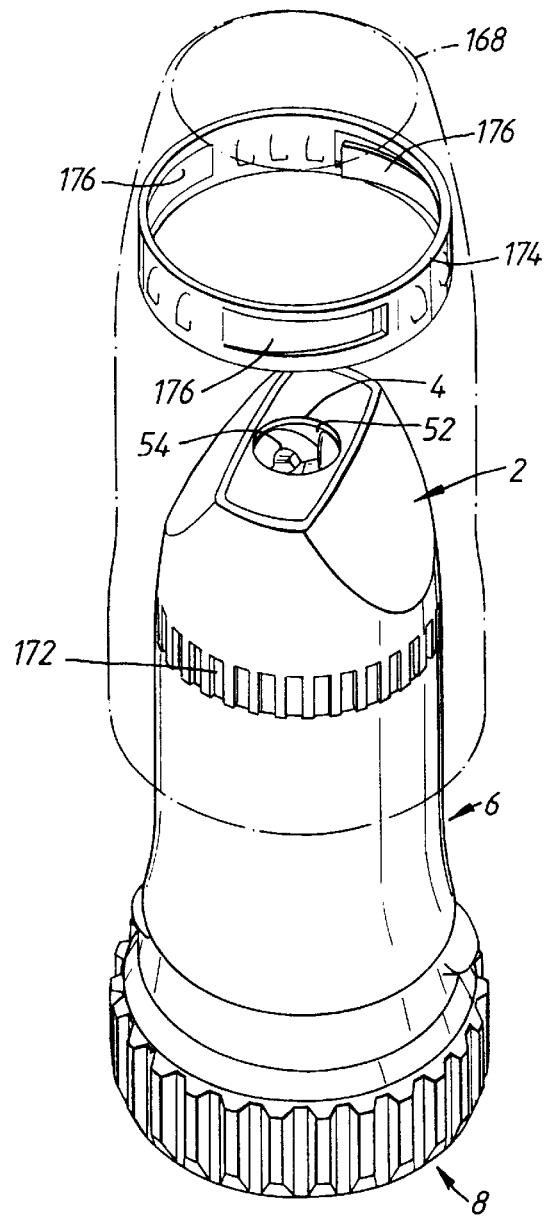
FIG. 17 illustrates the cap and the mouthpiece of a powder inhaler in accordance with a tenth embodiment of the present invention (with part of the cap illustrated in phantom)

FIG. 17 illustrates the cap and the mouthpiece of a powder inhaler in accordance with a tenth embodiment of the present invention. This embodiment incorporates an alternative construction for rotating the mouthpiece of an inhaler on removing the cap. In this embodiment a plurality of axially-directed grooves 172 are provided in the periphery of the mouthpiece 2 and the cap 168 is provided with an insert 174 disposed in an upper portion thereof. The insert 174 is in the shape of a ring and comprises a plurality of radially inwardly-biased members 176 which are configured to engage with the grooves 172 in the mouthpiece 2. The distal ends of the members 176 are directed in the counter-clockwise sense when viewed from above. In use, when the cap 168 is removed, in this embodiment by unscrewing in the counter-clockwise sense when viewed from above, the members 176 locate in respective grooves 172 and cause the mouthpiece 2 to be rotated relative to the inhaler body 6. In this way, whenever a user removes the cap 168 the mouthpiece 2 is automatically rotated. In fitting the cap 168, in this embodiment by screwing in the clockwise sense, the members 176 are deflected and ride over the grooves 172.

Figure 18:
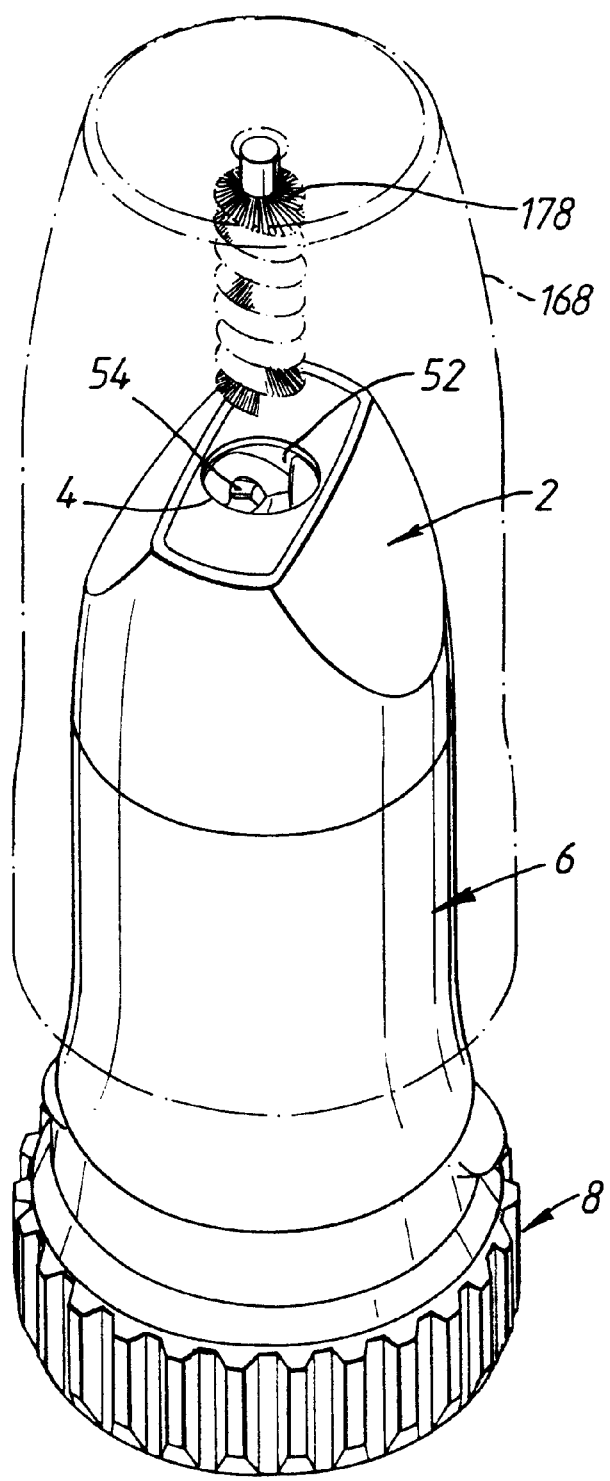
FIG. 18 illustrates a powder inhaler in accordance with an eleventh embodiment of the present invention (with part of the mouthpiece illustrated in phantom).

FIG. 18 illustrates a powder inhaler in accordance with an eleventh embodiment of the present invention. This embodiment is a modification of the above-described known powder inhaler. In this embodiment, similarly to the above-described known powder inhaler, the mouthpiece 2 comprises a tubular section 52, which includes one or more spirally or helically shaped projections 54 that act to deflect the air drawn therethrough and thereby deagglomerate any larger particles of entrained powder. This embodiment differs from the above-described known powder inhaler in comprising a cap 168 which includes a brush 178 that extends from the lower surface of the upper end thereof. The brush 178 is located along the longitudinal axis of the cap 168 such that when the cap 168 is fitted, in this embodiment by screwing in the clockwise sense, the brush 178 extends into the tubular section 52. In this way, whenever the cap 168 is fitted or removed, the brush 178 acts to dislodge powder which may have accumulated within the tubular section 52. In a preferred embodiment the brush 178 is formed in a spiral or helical shape so as more effectively to clean the surfaces of the spirally or helically shaped projections 54 within the tubular section 52. In another embodiment the brush 178 can be mounted to the cap 168 so as to allow relative rotation.

In further embodiments the present invention may provide inhalers in which vibrations are created using electrical power. In one embodiment a piezoelectric element can be used to create vibrations for dislodging powder which may have accumulated. The piezoelectric element can be driven by a battery or by movement of part of the inhaler, for example by rotation of the mouthpiece as described hereinabove. In another embodiment an electrostatic field can be used to dislodge powder which may have accumulated.

In yet further embodiments the present invention may provide inhalers in which vibrations are created by parts which cooperate. In one embodiment a detented surface may be provided between the mouthpiece and the inhaler body such that vibrations are created on relative axial movement thereof. In another embodiment the cap and the mouthpiece or the inhaler body can be provided with a detented surface therebetween such that on fitting the cap, for example by a push fit or a screw fit, vibrations are created.

Finally, it will be understood by a person skilled in the art that the present invention has been described in its preferred embodiments and can be modified in many different ways without departing from the scope of the invention as defined in the appended claims.

What is claimed is:

1. A powder inhaler for administering powder by inhalation, comprising:

a dosing unit for providing a dose of powder; and a flow path downstream of the dosing unit which is defined by a plurality of surfaces though which a stream of air entraining the dose of powder is in use drawn on inhalation by a user;

characterized in that at least one of the surfaces of the flow path is movable relative to at least one other of the surfaces of the flow path and in that the inhaler further comprises a powder dislodging member which is of fixed position relative to one of the at least one or at least one other of the surfaces of the flow path and is configured on relative movement of the at least one and one other of the surfaces of the flow path, to contact the other of the at least one or at least one other of the surfaces of the flow path such as to dislodge powder accumulated thereon.

2. The inhaler according to claim 1, wherein the flow path included a chamber which includes an inlet and an outlet.

3. The inhaler according to claim 2, wherein the other of the at least one or at least one other of the surfaces of the flow path defines at least part of the chamber.

4. The inhaler according to claim 3 wherein the at least one and the at least one other of the surfaces of the flow path define at least in part opposed surfaces of the chamber and include the inlet and the outlet thereto.

5. The inhaler according to claim 4 further comprising a storage chamber for storing a plurality of doses of powder, which storage chamber includes a filling inlet in one of the opposed surfaces of the chamber, and a plug for sealing the filling inlet of the storage chamber, which plug includes the powder dislodging member.

6. The inhaler according to claim 1 further comprising a mouthpiece which includes one of the at least one or at least one other of the surfaces of the flow path.

* * * * *